United States Patent
Lewandowski et al.

(10) Patent No.: US 8,084,515 B2
(45) Date of Patent: *Dec. 27, 2011

(54) DENTAL COMPOSITIONS CONTAINING CARBOSILANE POLYMERS

(75) Inventors: Kevin M. Lewandowski, Inver Grove Heights, MN (US); Ahmed S. Abuelyaman, Woodbury, MN (US); Todd D. Jones, St. Paul, MN (US); Babu N. Gaddam, Woodbury, MN (US); Sumita B. Mitra, West St. Paul, MN (US); Naimul Karim, Maplewood, MN (US); Adrian S. Eckert, Herrsching (DE); Peter Bissinger, Diessen (DE)

(73) Assignee: 3M Innovative Properties Company, Saint Paul, MN (US)

( * ) Notice: Subject to any disclaimer, the term of this patent is extended or adjusted under 35 U.S.C. 154(b) by 415 days.

This patent is subject to a terminal disclaimer.

(21) Appl. No.: 11/571,949

(22) PCT Filed: Jul. 13, 2005

(86) PCT No.: PCT/US2005/024821
§ 371 (c)(1),
(2), (4) Date: Oct. 26, 2007

(87) PCT Pub. No.: WO2006/019796
PCT Pub. Date: Feb. 23, 2006

(65) Prior Publication Data
US 2008/0045626 A1    Feb. 21, 2008

Related U.S. Application Data

(60) Provisional application No. 60/587,978, filed on Jul. 14, 2004.

(51) Int. Cl.
*A61K 6/083* (2006.01)
*A61K 6/093* (2006.01)
*C08G 77/02* (2006.01)
*C08G 77/60* (2006.01)
*C08G 77/00* (2006.01)

(52) U.S. Cl. ............... 523/116; 523/115; 433/228.1; 106/35; 528/25; 528/26; 528/32; 528/33; 528/35; 528/43

(58) Field of Classification Search ............... 523/116, 523/118, 115; 433/217.1, 222.1, 228.1; 528/31, 528/43, 25, 26, 32, 33, 35; 106/35
See application file for complete search history.

(56) References Cited

U.S. PATENT DOCUMENTS

| | | |
|---|---|---|
| 3,159,601 A | 12/1964 | Ashby |
| 3,220,972 A | 11/1965 | Lamoreaux |
| 3,419,593 A | 12/1968 | Willing |
| 3,715,334 A | 2/1973 | Karstedt |
| 3,775,352 A | 11/1973 | Leonard, Jr. |
| 3,775,452 A | 11/1973 | Karstedt |
| 3,814,730 A | 6/1974 | Karstedt |
| 3,927,116 A | 12/1975 | Rick et al. |
| 3,933,880 A | 1/1976 | Bergstrom et al. |
| 3,971,754 A | 7/1976 | Jurecic |
| 4,071,424 A | 1/1978 | Dart et al. |
| 4,288,345 A | 9/1981 | Ashby et al. |
| 4,356,296 A | 10/1982 | Griffith et al. |
| 4,391,590 A | 7/1983 | Dougherty |
| 4,421,903 A | 12/1983 | Ashby |
| 4,503,169 A | 3/1985 | Randklev |
| 4,510,094 A | 4/1985 | Drahnak |
| 4,530,879 A | 7/1985 | Drahnak |
| 4,563,514 A | 1/1986 | Liu |
| 4,600,484 A | 7/1986 | Drahnak |
| 4,603,215 A | 7/1986 | Chandra et al. |
| 4,642,126 A | 2/1987 | Zador et al. |
| 4,652,274 A | 3/1987 | Boettcher et al. |
| 4,665,217 A | 5/1987 | Reiners et al. |
| 4,695,251 A | 9/1987 | Randklev |
| 4,705,765 A | 11/1987 | Lewis |
| 4,706,765 A | 11/1987 | Lee et al. |
| 4,752,338 A | 6/1988 | Reiners et al. |
| 4,767,798 A | 8/1988 | Gasser et al. |
| 4,771,530 A | 9/1988 | Creedon |
| 4,772,530 A | 9/1988 | Gottschalk et al. |
| 4,788,268 A | 11/1988 | Lau et al. |
| 4,874,450 A | 10/1989 | Gottschalk et al. |
| 4,882,365 A | 11/1989 | Gasser et al. |
| 4,954,414 A | 9/1990 | Adair et al. |
| 5,026,902 A | 6/1991 | Fock et al. |
| 5,055,372 A | 10/1991 | Shanklin et al. |
| 5,057,393 A | 10/1991 | Shanklin et al. |

(Continued)

FOREIGN PATENT DOCUMENTS

EP    0 173 567 A2    3/1986

(Continued)

OTHER PUBLICATIONS

ANSI/ADA specification No. 27 (1993).

(Continued)

*Primary Examiner* — Michael Pepitone
(74) *Attorney, Agent, or Firm* — Pamela L. Stewart

(57) ABSTRACT

Carbosilane-containing polymers (including oligomers) having the following structural features: greater than one repeat unit; at least four Si-arylene bonds; at least one (meth)acrylate moiety, Si—H moiety, or both; no Si—O bonds; preferably at least four silicon atoms; wherein two silicon atoms are separated by one arylene group in each repeat unit.

10 Claims, No Drawings

U.S. PATENT DOCUMENTS

| | | |
|---|---|---|
| 5,076,844 A | 12/1991 | Fock et al. |
| 5,145,886 A | 9/1992 | Oxman et al. |
| 5,165,890 A | 11/1992 | Discko, Jr. |
| 5,233,006 A | 8/1993 | Wolter et al. |
| 5,322,440 A | 6/1994 | Steele |
| 5,346,980 A | 9/1994 | Babu |
| 5,399,738 A | 3/1995 | Wolter et al. |
| 5,532,398 A | 7/1996 | Wolter et al. |
| 5,545,676 A | 8/1996 | Palazzotto et al. |
| 5,691,433 A | 11/1997 | Kotani |
| 6,046,250 A | 4/2000 | Boardman et al. |
| 6,245,828 B1 | 6/2001 | Weinmann et al. |
| 6,376,569 B1 | 4/2002 | Oxman et al. |
| 6,387,981 B1 | 5/2002 | Zhang et al. |
| 6,562,953 B2 | 5/2003 | Dhainaut et al. |
| 6,566,413 B1 | 5/2003 | Weinmann et al. |
| 6,572,693 B1 | 6/2003 | Wu et al. |
| 6,624,211 B2 | 9/2003 | Karim et al. |
| 6,624,236 B1 | 9/2003 | Bissinger et al. |
| 6,653,375 B2 | 11/2003 | Moszner et al. |
| 6,852,822 B1 | 2/2005 | Bissinger et al. |
| 7,915,324 B2 * | 3/2011 | Eckert et al. .................. 523/116 |
| 2002/0013454 A1 | 1/2002 | Dhainaut et al. |
| 2002/0115743 A1 | 8/2002 | Karim et al. |
| 2003/0035899 A1 | 2/2003 | Klettke et al. |
| 2003/0152601 A1 | 8/2003 | Kanayama |
| 2003/0166816 A1 | 9/2003 | Bissinger et al. |
| 2003/0181541 A1 | 9/2003 | Wu et al. |
| 2003/0236342 A1 | 12/2003 | Walz et al. |
| 2004/0082683 A1 | 4/2004 | Karim et al. |
| 2004/0186202 A1 | 9/2004 | Klettke et al. |
| 2004/0209990 A1 | 10/2004 | Walz et al. |
| 2005/0013842 A1 | 1/2005 | Qiu et al. |
| 2005/0252413 A1 | 11/2005 | Kangas et al. |
| 2005/0252414 A1 | 11/2005 | Craig et al. |
| 2005/0256223 A1 | 11/2005 | Kolb et al. |
| 2007/0276059 A1 * | 11/2007 | Lewandowski et al. ...... 523/116 |

FOREIGN PATENT DOCUMENTS

| | | |
|---|---|---|
| EP | 0 201 031 A2 | 11/1986 |
| EP | 0 201 778 A1 | 11/1986 |
| EP | 0 238 025 A2 | 9/1987 |
| EP | 0 238 025 A3 | 9/1987 |
| EP | 0 201 778 B1 | 12/1988 |
| EP | 0 201 031 B1 | 8/1989 |
| EP | 0 373 384 A1 | 6/1990 |
| EP | 0 451 709 A2 | 10/1991 |
| EP | 0 373 384 B1 | 10/1992 |
| EP | 0 238 025 B1 | 12/1992 |
| EP | 0 661 331 A2 | 7/1995 |
| EP | 0 451 709 B1 | 12/1999 |
| EP | 1 368 402 A1 | 12/2003 |
| EP | 1 368 402 B1 | 8/2004 |
| JP | 61-258838 | 11/1986 |
| JP | 07-309879 | 11/1995 |
| JP | 11-092563 | 4/1999 |
| JP | 11-199677 | 7/1999 |
| WO | WO 8601219 A1 * | 2/1986 |
| WO | 00/38619 A2 | 7/2000 |
| WO | 00/38619 A3 | 7/2000 |
| WO | 00/42092 A1 | 7/2000 |
| WO | 01/07444 A1 | 2/2001 |
| WO | 01/30305 A1 | 5/2001 |
| WO | 01/30306 A1 | 5/2001 |
| WO | 01/30307 A1 | 5/2001 |
| WO | 01/92271 A1 | 12/2001 |
| WO | 01/92281 A1 | 12/2001 |
| WO | 01/95862 A1 | 12/2001 |
| WO | 01/95865 A1 | 12/2001 |
| WO | 02/066535 A1 | 8/2002 |
| WO | 03/063804 A1 | 8/2003 |
| WO | 2006/005363 A1 | 1/2006 |
| WO | 2006/005366 A1 | 1/2006 |
| WO | 2006/019796 | 2/2006 |
| WO | 2006/019801 | 2/2006 |

OTHER PUBLICATIONS

Beck et al., Phenenyl Silicon Compounds, *J. Chem. Eng. Data*, 1963, 8(3), 453-454.

Houben-Weyl, *Methoden der Organischen Chemie*, vol. VI/3, pp. 56, 57, Georg Thieme Verlag, Stuttgart, 1965, 4th Edition.

Houben-Weyl, *Methoden der Organischen Chemie*, vol. X111/2a, pp. 47-192, Georg Thieme Verlag, Stuttgart, 1973, 4th Edition.

ISO 4049, Mar. 1994.

ISO 9917, Nov. 1, 2003.

Tarbell et al., The Rearrangement of 4-Crotyloxy-3,5-Dichlorobenzoic Acid, *J. Am. Chem. Soc.*, 1942, 64(5), 1066-1070.

Marciniec, *Comprehensive Handbook on Hydrosilylation*, pp. 8ff, 107ff, and 151ff, Pergamon Press, Oxford, 1992.

Watts shrinkage test procedure (3M test method DTS-1303), Jul. 14, 2003.

Watts et al., Kinetic Measurement of Photo-Polymerization Contraction in Resins and Composites, *Meas. Sci. Technol.*, 2, 788-794 (1991).

U.S. Appl. No. 09/541,417 (Karim) "Dental Materials with Extendable work Time Kits, and Methods," filed Apr. 3, 2000.

U.S. Appl. No. 60/587,762 "Dental Compositions Containing Carbosilane Monomers," filed on Jul. 14, 2004.

Tsumura, Manabu, et al., "Synthesis and Properties of Polycarbosilanes with the Meta-Linkage Bending Unit by Hydrosilylation Polymerization", Table 1, Oct. 25, 1996, pp. 3156-3157 and Journal of Polymer Science, Part A: Polymer Chemistry, 3155-3161 34(15).

* cited by examiner

DENTAL COMPOSITIONS CONTAINING CARBOSILANE POLYMERS

CROSS REFERENCE TO RELATED APPLICATIONS

This application is a national stage filing under 35 U.S.C. 371 of PCT/US2005/024821 filed Jul. 13, 2005, which claims the benefit of U.S. Provisional Application No. 60/587,978, filed Jul. 14, 2004, the disclosure of which is incorporated by reference in its entirety herein.

FIELD OF THE INVENTION

Carbosilane polymers and dental compositions comprising such polymers.

BACKGROUND

It is well known that the volume shrinkage of dental compositions upon curing results in high stress and micro fractures in the composite. Such defects may lead to clinical failure of the composite material. Therefore, it is important to develop dental composites with a reduced volume shrinkage while maintaining the outstanding physical properties of current materials.

Current commercial (meth)acrylate-based composites exhibit a volume shrinkage of 2-4 percent (%) upon polymerization. The goal is to reduce the shrinkage below 2% while maintaining other desirable physical properties, such as compressive strength and viscosity. Although many types of components have been developed for use in dental composites, particularly (meth)acrylate-based composites, to reduce polymerization shrinkage, composites based on them generally suffer from reduced physical properties compared to commercial products, such as that available from 3M Company, St. Paul, Minn. under the trade designation FILTEK Z250.

Thus, there is still a need for new components that can be added to (meth)acrylate-based dental compositions that provide reduced shrinkage.

SUMMARY OF THE INVENTION

The present invention provides carbosilane polymers for use in dental compositions. The carbosilane polymers (i.e., carbosilane-containing polymers) are materials with more than one repeat unit. Herein, polymers and polymeric materials include within their scope relatively low molecular weight oligomeric materials. Preferably, the carbosilane polymers include carbosilane-containing oligomeric materials. Such materials preferably include the following structural features: greater than one repeat unit; at least 4 Si-arylene bonds; at least 1 (meth)acrylate moiety, Si—H moiety, or both; no Si—O bonds; and preferably at least 4 silicon atoms. Such materials typically also include 2 silicon atoms separated by one arylene group in each repeat unit.

In certain embodiments, the carbosilane polymers are formed from the reaction of aromatic silanes, particularly arylene disilanes, and ethylenically unsaturated compounds. These materials may be crystallizable or non-crystallizable, depending on the desired balance of the properties before and after hardening the composition. Dental compositions that include these materials typically and preferably have a lower volume shrinkage upon hardening. Also, the resultant hardened composites have potentially higher stain resistance compared to current composites.

Dental compositions of the present invention also typically include an initiator system, such as a photoactive free radical source (preferably one activated by blue light). In certain embodiments, dental compositions also include a filler system, preferably up to 80 percent by weight (i.e., wt-%) of a filler system (preferably including an inorganic filler), based on the total weight of the composition. Other optional ingredients include, for example, a colorant, a flavoring agent, a medicament, a stabilizer, a viscosity modifier, a diluting agent, a flow control additive, a thixotropic agent, an antimicrobial, and a polymeric thickener. Various combinations of each of the components listed herein can be used for desired effect.

In certain embodiments, the carbosilane polymers of the present invention have the following Formula (I):

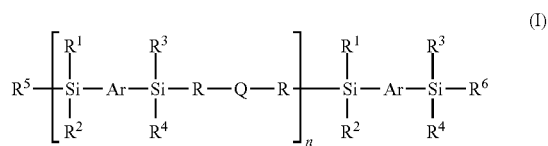

wherein:
  each Ar is independently an arylene group;
  each R is independently an aliphatic group, cycloaliphatic group, or combinations thereof, optionally including one or more O, Br, Cl, or Si atoms, or combinations thereof, which can include a bicyclic group;
  each Q is independently a bond, or an aliphatic group, cycloaliphatic group, aromatic group, or combinations thereof, optionally including one or more O, Br, Cl, or Si atoms, or combinations thereof, which can include a bicyclic group, wherein Q optionally includes one or more (meth)acrylate groups;
  each $R^1$-$R^4$ group is independently an aliphatic group, cycloaliphatic group, aromatic group, or combinations thereof, optionally substituted by one or more (meth)acrylate groups;
  each $R^5$-$R^6$ group is independently hydrogen, an aliphatic group, cycloaliphatic group, aromatic group, or combinations thereof, optionally substituted by one or more (meth)acrylate groups; and
  n is greater than 1.

In certain embodiments, the carbosilane polymers of the present invention have the following Formula (II):

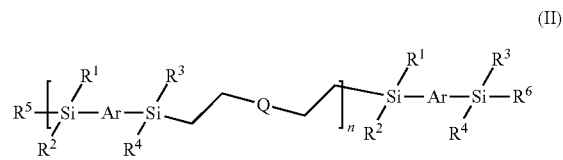

wherein:
  each Ar is independently an arylene group;
  each Q is independently a bond, or an aliphatic group, cycloaliphatic group, aromatic group, or combinations thereof, optionally including one or more O, Br, Cl, or Si atoms, or combinations thereof, which can include a bicyclic group, wherein Q is optionally substituted with one or more (meth)acrylate groups;
  each $R^1$-$R^4$ group is methyl;
  each $R^5$-$R^6$ group is independently hydrogen, an aliphatic group, cycloaliphatic group, aromatic group, or combinations thereof, optionally including one or more O, Br, Cl, or Si atoms, or combinations thereof, and optionally substituted by one or more (meth)acrylate groups; and n is greater than 1.

DEFINITIONS

The term "hardenable" refers to a material that can be cured or solidified, e.g., by heating to remove solvent, heating to cause polymerization, chemical crosslinking, radiation-induced polymerization or crosslinking, or the like.

The term "arylene" as used herein includes carbocyclic aromatic rings or ring systems, wherein the aromatic rings can be optionally bridged by oxygen, nitrogen, sulfur, or alkylene groups, or combinations thereof, and optionally substituted with halogen, alkyl or alkoxy groups, or combinations thereof. Examples of arylene groups include phenylene, naphthylene, biphenylene, fluorenylene, indenylene, diphenylene ether, optionally substituted with alkyl and/or alkoxy groups.

By "crystallizable" it is meant that the material either alone or in the presence of other monomers displays a crystalline melting point at 20° C. or above when measured by differential scanning calorimetry (DSC). The peak temperature of the observed endotherm is taken as the crystalline melting point. The crystalline phase includes multiple lattices in which the material assumes a conformation in which there is a highly ordered registry in adjacent chemical moieties of which the material is constructed. The packing arrangement (short order orientation) within the lattice is highly regular in both its chemical and geometric aspects. A crystallizable component may be in a "semicrystalline state" in that long segments of polymer chains appear in both amorphous and crystalline states or phases at 20° C. or above. Thus, herein a "crystallizable" component encompasses semicrystalline materials.

The term "non-crystallizable" means materials that are composed of randomly orientated atoms, ions, or molecules that do not form defined patterns, lattice structures, or long range order (i.e., amorphous). Non-crystallizable materials do not display a crystalline melting point at 20° C. or above when measured by differential scanning calorimetry (DSC).

The terms "comprises" and variations thereof do not have a limiting meaning where these terms appear in the description and claims.

As used herein, "a," "an," "the," "at least one," and "one or more" are used interchangeably. Thus, for example, a dental composition that comprises "a" carbosilane-containing component can be interpreted to mean that the dental composition includes "one or more" carbosilane-containing components. Similarly, a composition comprising "a" filler can be interpreted to mean that the composition includes "one or more" types of fillers.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

The present invention provides carbosilane polymers (including oligomers) for use in dental compositions, particularly with other (meth)acrylate-based components. The carbosilane polymers (i.e., carbosilane-containing polymers) preferably include the following structural features: greater than one repeat unit; at least 2 Si-arylene bonds; at least 1 (meth)acrylate moiety, Si—H moiety, or both (preferably, having at least 2 (meth)acrylate moieties); no Si—O bonds; and preferably at least 4 Si atoms; wherein 2 silicon atoms are separated by one arylene group in each repeat unit.

Significantly, these aromatic carbosilane polymers can be prepared using simple hydrosilation procedures, for example. The wide availability of starting materials (e.g., aromatic silanes, or more specifically arylene disilanes, and ethylenically unsaturated, or more specifically diolefin, compounds) allows for broad control over the structure, architecture, and functionality of the carbosilane component. Thus, typically, the repeat unit of the carbosilane component includes a chemical moiety derived from the reaction product of an ethylenically unsaturated compound (typically, a diolefin compound) and an arylene disilane (with 2 Si—H moieties). Through this chemistry, it is possible to prepare, preferably in one step, linear materials with polymerizable functionality (preferably, (meth)acrylate functionality) along the main chain.

Carbosilane Component and Preparation Thereof

The materials of the carbosilane component are typically polymeric, and preferably, oligomeric. That is, a carbosilane component includes one or more polymerizable polymers, preferably oligomers.

Thus, "polymer" and "polymeric" are used herein to refer to any materials having more than one repeat unit, thereby encompassing oligomers. Thus, unless otherwise specified, polymers include oligomers, which are generally of a molecular weight of 20,000 grams per mole or less. Furthermore, the term polymer is used herein to encompass both homopolymers and copolymers, and the term copolymer is used herein to encompass materials with two or more different repeat units (e.g., copolymers, terpolymers, tetrapolymers).

The molecular weight and viscosity of the polymeric material can be easily controlled by simply changing the building blocks used in the reaction. The number average molecular weight of the carbosilane materials may vary over a broad range. Preferably, the molecular weight is no greater than 20,000 grams per mole (g/mol), however, if the materials are polymeric, the molecular weight can be higher. More preferably, number average molecular weight of the carbosilane materials is no greater than 10,000 grams per mole (g/mol), and even more preferably no greater than 5000 g/mol. Preferably, the molecular weight is at least 500 g/mol, and more preferably at least 750 g/mol. The starting materials for the polymerization can be chosen to give final products that are liquids or solids at room temperature.

A preferred carbosilane component is hardenable (e.g., polymerizable and/or crosslinkable), preferably by a free radical mechanism. The carbosilane polymer may or may not be crystallizable.

The carbosilane polymers (i.e., carbosilane-containing polymers) preferably include the following structural features: greater than one repeat unit; at least 2 Si-arylene bonds; at least 1 (meth)acrylate moiety, Si—H moiety, or both; no Si—O bonds; and preferably at least 4 Si atoms; wherein 2 silicon atoms are separated by one arylene group in each repeat unit. Preferably, the carbosilane polymer has a functionality greater than one, more preferably at least two. Preferably, the carbosilane polymer has at least 2 (meth)acrylate moieties.

Preferably, the carbosilane component has the following (Formula I):

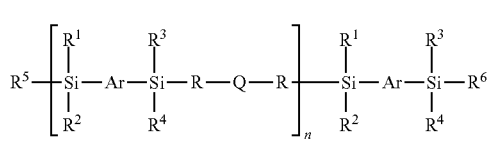

(I)

wherein:
  each Ar is independently an arylene group;
  each R is independently an aliphatic group, cycloaliphatic group, or combinations thereof, optionally including one or more O, Br, Cl, or Si atoms, or combinations thereof, which can include a bicyclic group;
  each Q is independently a bond, or an aliphatic group, cycloaliphatic group, aromatic group, or combinations thereof, optionally including one or more O, Br, Cl, or Si atoms, or combinations thereof, which can include a bicyclic group, wherein Q optionally includes one or more (meth)acrylate groups;
  each $R^1$-$R^4$ group is independently an aliphatic group, cycloaliphatic group, aromatic group, or combinations thereof, optionally substituted by one or more (meth)acrylate groups;
  each $R^5$-$R^6$ group is independently hydrogen, an aliphatic group, cycloaliphatic group, aromatic group, or combinations thereof, optionally substituted by one or more (meth)acrylate groups; and
  n (which is an average value) is greater than 1, and preferably, 2 or more.

The term "arylene" as used herein includes carbocyclic aromatic rings or ring systems, wherein the aromatic rings can be optionally bridged by oxygen, nitrogen, sulfur, or alkylene groups, or combinations thereof, and optionally substituted with halogen, alkyl or alkoxy groups, or combinations thereof. Examples of arylene groups include phenylene, naphthylene, biphenylene, fluorenylene, indenylene, diphenylene ether, optionally substituted with alkyl and/or alkoxy groups.

Preferably, in Formula I, each arylene (Ar) group independently has 6-14 carbon atoms in the ring system, optionally substituted by one or more halogen and/or alkyl groups (wherein the alkyl preferably has 1-10 carbon atoms, and more preferably 1-6 carbon atoms). In the ring system aromatic groups can be optionally bridged by oxygen and/or alkylene groups. More preferably, arylene is phenylene or diphenylene ether (—$C_6H_4$—O—$C_6H_4$—), optionally substituted with one or more halogen and/or (C1-C3)alkyl groups.

Preferably, in Formula I, each R is ethylene.

For certain embodiments in Formula I, each Q is independently and preferably —$CH_2$—O—Ar'—O—$CH_2$—, wherein Ar' is an arylene group having 6-14 carbon atoms, optionally substituted by one or more halogen and/or alkyl groups (wherein the alkyl preferably has 1-10 carbon atoms, and more preferably 1-6 carbon atoms). In the ring system aromatic groups can be optionally bridged by oxygen and/or alkylene groups.

For certain embodiments of Formula I, each Q is independently and preferably —$CH_2$—O-alkylene-O—$CH_2$— wherein the alkylene (preferably, a C1-C4 alkylene) is substituted with a (meth)acrylate group.

Preferably, in Formula I, each $R^1$-$R^4$ group is independently an aliphatic group having 1-6 carbon atoms, cycloaliphatic group having 1-6 carbon atoms, an aromatic group having 6-14 carbon atoms, or combinations thereof. More preferably, each $R^1$-$R^4$ group is independently an aliphatic group having 1-6 carbon atoms (and more preferably, 1-3 carbon atoms).

Preferably, in Formula I, each $R^5$-$R^6$ group is independently hydrogen, an aliphatic group having 1-10 carbon atoms, cycloaliphatic group having 1-10 carbon atoms, an aromatic group having 6-14 carbon atoms, or combinations thereof, optionally substituted by one or more (meth)acrylate groups, and including one or more O, Br, Cl, or Si atoms, or combinations thereof, which can include a bicyclic group. More preferably, each $R^5$-$R^6$ group is independently hydrogen or an aliphatic group having 1-10 carbon atoms (and more preferably, 1-3 carbon atoms), substituted by one or more (meth)acrylate groups.

More preferably, the carbosilane component has the following (Formula II):

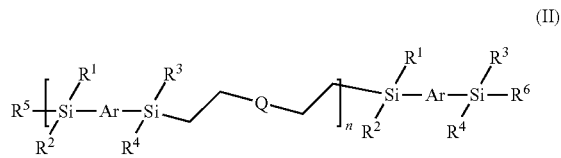

(II)

wherein:
  each Ar is independently an arylene group;
  each Q is independently a bond, or an aliphatic group, cycloaliphatic group, aromatic group, or combinations thereof, optionally including one or more O, Br, Cl, or Si atoms, or combinations thereof, which can include a bicyclic group, wherein Q is optionally substituted with one or more (meth)acrylate groups;
  each $R^1$-$R^4$ group is methyl;
  each $R^5$-$R^6$ group is independently hydrogen, an aliphatic group, cycloaliphatic group, aromatic group, or combinations thereof, optionally including one or more O, Br, Cl, or Si atoms, or combinations thereof, and optionally substituted by one or more (meth)acrylate groups; and
  n (which is an average value) is greater than 1, and preferably, 2 or more.

In Formula II, arylene is defined as above. Preferably, each arylene (Ar) group independently has 6-14 carbon atoms in the ring system, optionally substituted by one or more halogen and/or alkyl groups (wherein the alkyl preferably has 1-10 carbon atoms, and more preferably 1-6 carbon atoms). In the ring system aromatic groups can be optionally bridged by oxygen and/or alkylene groups. More preferably, arylene is phenylene or diphenylene ether (—$C_6H_4$—O—$C_6H_4$—), optionally substituted with one or more halogen and/or (C1-C3)alkyl groups.

For certain embodiments of Formula II, each Q is independently and preferably —$CH_2$—O—Ar'—O—$CH_2$—, wherein Ar' is an arylene group having 6-14 carbon atoms, optionally substituted by one or more halogen and/or alkyl groups (wherein the alkyl preferably has 1-10 carbon atoms, and more preferably 1-6 carbon atoms). In the ring system aromatic groups can be optionally bridged by oxygen and/or alkylene groups.

For certain embodiments of Formula II, each Q is independently and preferably —$CH_2$—O-alkylene-O—$CH_2$— wherein the alkylene (preferably, a C1-C4 alkylene) is substituted with a (meth)acrylate group.

Preferably, in Formula II, each $R^5$-$R^6$ group is independently hydrogen, an aliphatic group having 1-10 carbon atoms, cycloaliphatic group having 1-10 carbon atoms, an aromatic group having 6-14 carbon atoms, or combinations thereof, optionally substituted by one or more (meth)acrylate groups, and including one or more O, Br, Cl, or Si atoms, or combinations thereof, which can include a bicyclic group. More preferably, each $R^5$-$R^6$ group is independently hydrogen or an aliphatic group having 1-10 carbon atoms (and more preferably, 1-3 carbon atoms), substituted by one or more (meth)acrylate groups.

The carbosilane component can be formulated into dental composites that exhibit a total volumetric polymerization shrinkage of no greater than 2.0% (typically, a shrinkage of 1.4% to 2.0%), wherein the percentage is based on the volume of the composition prior to hardening, while preferably maintaining excellent physical properties.

Preferably, the total amount of the carbosilane component in a dental composition is at least 1 wt-%, more preferably, at least 3 wt-%, and most preferably, at least 5 wt-%, based on the total weight of the composition. Preferably, the total amount of the carbosilane component is no greater than 60 wt-%, more preferably, no greater than 50 wt-%, and most preferably, no greater than 40 wt-%, based on the total weight of the composition.

Scheme 1 outlines a preferred general procedure for the preparation of a carbosilane-containing material. Such materials can be prepared with polymerizable end groups, and optionally, polymerizable groups pendant from the main chain of the polymer.

Although Scheme 1 is shown using a bis(dimethylsilyl)-arylene, substituents other than methyl can be used in the arylene disilane reactant. Similarly, although Scheme 1 is shown using a diolefin, other ethylenically unsaturated reactants can be used, including (meth)acrylate compounds. Furthermore, although Scheme 1 shows a methacrylate functional olefin reactant in the end-capping step of the scheme, acrylates can be used as well as other ethylenically unsaturated compounds. Preferably, one of the reactants includes a (meth)acrylate (i.e., acrylate or methacrylate) moiety.

having 1-10 carbon atoms, cycloaliphatic group having 1-10 carbon atoms, or an aromatic group having 6-14 carbon atoms. More preferably, R' is an aliphatic group having 1-10 carbon atoms (and more preferably, 1-3 carbon atoms).

As shown in Scheme 1, a difunctional aromatic silane is reacted with a difunctional ethylenically unsaturated compound through a hydrosilation reaction, resulting in a polymeric (and preferably, oligomeric) product. The intermediate can then be reacted with a (meth)acrylate functional ethylenically unsaturated compound to give a polymerizable polymer (preferably, oligomer) with methacrylate end groups. The stoichiometry of the initial reaction is typically chosen so that the polymer has silyl (Si—H) end groups that can be further functionalized with (meth)acrylate functional ethylenically unsaturated compounds. Alternatively, the difunctional aromatic silane and/or diolefin compound may also contain polymerizable groups, resulting in polymers with polymerizable groups pendent from the backbone of the chain. The stoichiometry can be chosen to produce silane or vinyl end groups, for example.

Typically, the starting aromatic silane and ethylenically unsaturated starting materials and a hydrosilation catalyst are reacted together in a solvent, typically at room temperature. The optional end capping compound is then added to the mixture. The catalyst can then be removed by filtration through silica gel to give the product, or the product can be obtained via crystallization or precipitation.

The hydrosilation catalyst used in the reaction can be any compound that will catalyze the addition reaction of silicon-bonded hydrogen atoms with compounds containing olefinic double bonds, for example. Examples of hydrosilation catalysts suitable for the composition of this invention include many of the late transition elements, such as cobalt, rhodium, iridium, nickel, palladium, and platinum, and their organometallic complexes. Preferred catalysts are those containing the metal platinum, such as finely divided platinum metal, platinum metal on a finely divided carrier, such as charcoal or alumina, and compounds of platinum, such as chloroplatinic acid, platinum olefin complexes, such as those described in U.S. Pat. No. 3,159,601; platinum alkyne complexes, such as

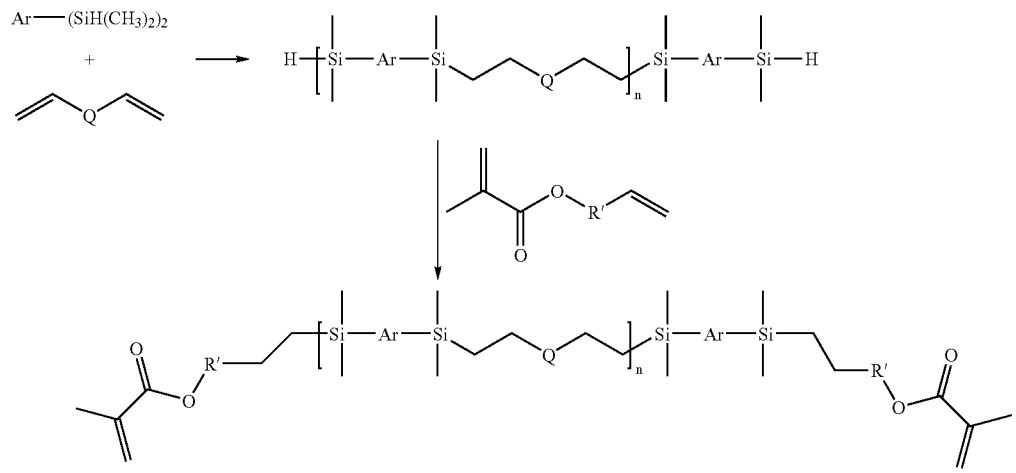

Scheme 1

In Scheme 1, Ar, Q, and n are defined above. R' represents an aliphatic group, cycloaliphatic group, aromatic group, or combinations thereof, optionally including one or more O, Br, Cl, and Si atoms, which is preferably an aliphatic group those described in U.S. Pat. No. 4,603,215; the reaction product of chloroplatinic acid with a member selected from the class consisting of alcohols, ethers, aldehydes, and mixtures thereof, such as those described in U.S. Pat. No. 3,220,972;

and the reaction product of chloroplatinic acid with tetravinylcyclotetrasiloxanes in the presence of sodium bicarbonate in ethanol solution, such as those described in U.S. Pat. No. 3,715,334. Particularly preferred catalysts are the complexes prepared with chloroplatinic acid and certain unsaturated organosilicon compounds, such as those described in U.S. Pat. Nos. 3,419,593; 3,775,452; 4,288,345; and 4,421,903. One specific example of these catalysts is the reaction product of chloroplatinic acid and sym-divinyltetramethyldisiloxane. Another particularly preferred catalyst is a colloidal hydrosilation catalyst obtained by the reaction between a silicon hydride or a siloxane hydride and a platinum(0) or platinum (II) complex, such as those described in U.S. Pat. No. 4,705,765. Still other particularly preferred catalysts are those that are activated by actinic radiation, such as the ($\eta^4$-1,5-cyclooctadiene) diarylplatinum and the ($\eta^5$-cyclopentadienyl) trialiphaticplatinum complexes described in U.S. Pat. Nos. 4,530,879; 4,510,094; and 4,600,484.

The catalyst should be present in an effective amount, i.e., an amount sufficient to catalyze the hydrosilation reaction. Satisfactory results may be obtained when the catalyst is present in an amount sufficient to provide as little as one part by weight of metal (e.g., platinum) per million parts by weight of the total composition. On the other hand, an amount of the catalyst sufficient to provide as high as 1 part to 10 parts by weight of metal (e.g., platinum) per 1,000 parts by weight of the total composition may also be used. In general, however, it is preferred to employ the catalyst in an amount sufficient to provide one to two hundred parts by weight of metal (e.g., platinum) per one million parts by weight of the total composition.

The aromatic silane starting materials can typically be prepared via the Grignard reaction between halogenated aromatic compounds and chloro-dimethyl silane (or other chloro-alkyl silanes) as disclosed in H. N. Beck et al., *J. Chem. Eng. Data*, 8, 453 (1963). Preferred aromatic silane starting materials include 1,4-bis-dimethylsilyl benzene, 1,3-bis-dimethylsilyl benzene, and bis-(p-dimethylsilyl)phenylether.

Suitable difunctional ethylenically unsaturated precursors include 1,4-bis(allyloxy)benzene, 1,3-bis(allyloxy)benzene, bisphenol A diallylether or tetrabromo bisphenol A diallylether, which are commercially available or can be synthesized from methods known in the art. For example, aryl alkyl ether compounds like allyl-phenyl-ether or but-2-enyl-(2-methoxy-phenyl)-ether were prepared according to Houben-Weyl, Methoden der Organischen Chemie, volume VI/3, p 57 (first preparation example) or p 56 (first preparation example), Georg Thieme Verlag, Stuttgart, 1965, 4th edition; or compounds like allyl-(2-chloro-phenyl)-ether as described by D. Tarbell et al., *J. Am. Chem. Soc.* 64(5), 1066-1070 (1942).

The difunctional ethylenically unsaturated precursors can be aromatic or aliphatic. Preferred aromatic compounds contain allyloxy substitution of an aromatic ring system. Also, the vinyl compounds can contain methacrylate functionality.

If desired, the end groups of the polymers (formed in the first step of Scheme 1) may be further reacted with mono- or multi-functional groups (in the second step of Scheme 1). If a molar excess of carbosilane functional groups are utilized in the polymerization (in the first step of Scheme 1), the polymer will contain carbosilane end groups that are capable of further reaction with compounds containing ethylenically unsaturated groups. If a molar excess of ethylenically unsaturated functional groups are utilized in the polymerization, the polymer will contain ethylenically unsaturated end groups that are capable of further reaction with compounds containing carbosilane groups. Typically, the polymerizations are performed with a molar excess of carbosilane groups that are further reacted with ethylenically unsaturated (meth)acrylate compounds in an end-capping reaction (the second step in Scheme 1). The ethylenically unsaturated substituted (meth) acrylate components typically contain one olefin group and at least one (meth)acrylate group. Preferred such compounds include allyl methacrylate, 2-(5/6-methacryloyloxy-bicyclo[2.2.1]hept-2-yl)-ethene, and (2-allyloxyethyl)methacrylate.

Schemes 2-5 generally follow Scheme 1 and outline the preparation scheme for preferred examples of carbosilane polymers, wherein Ar and n are as defined above.

Scheme 2

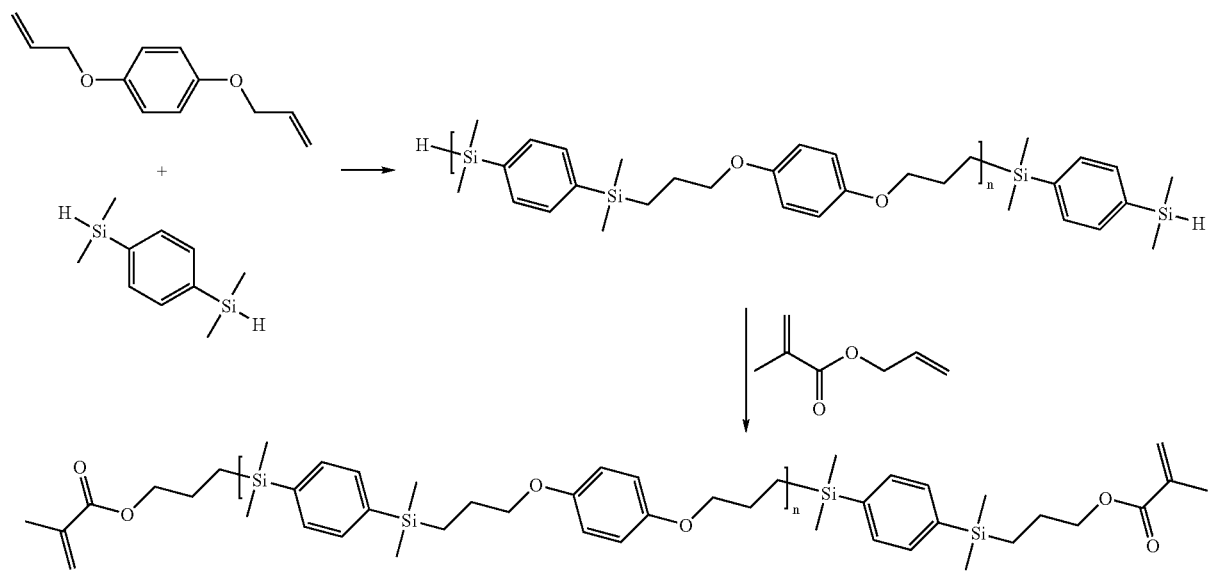

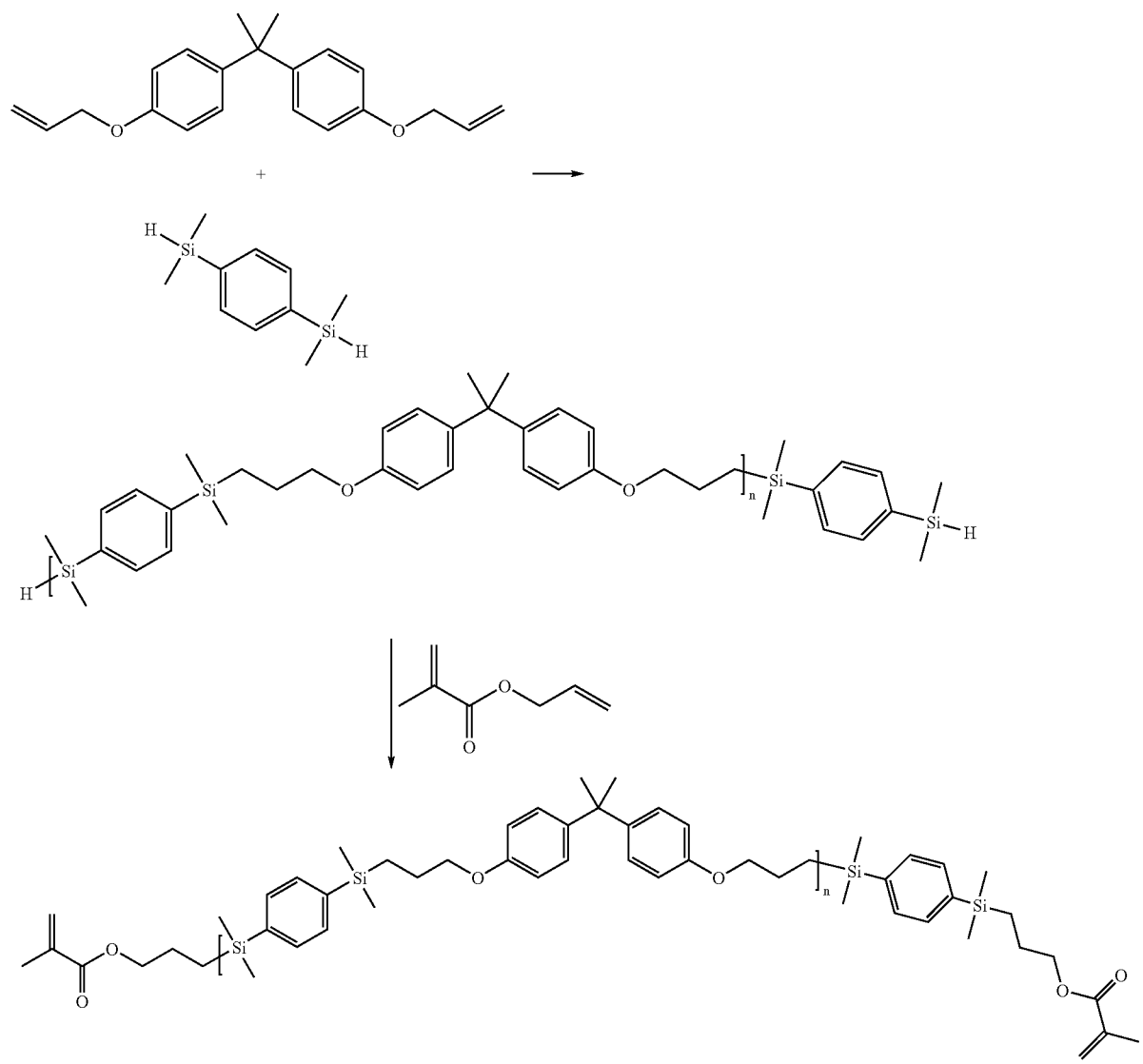
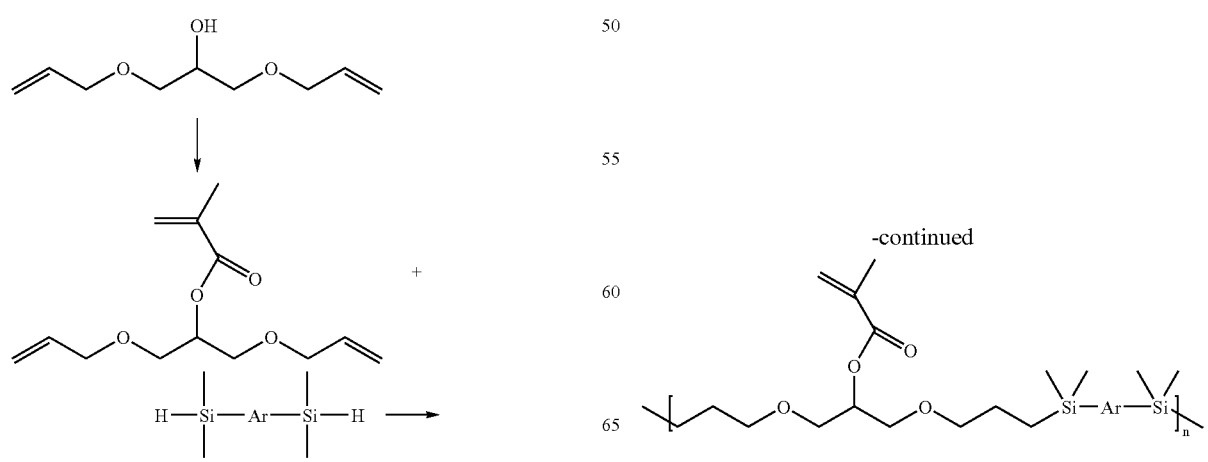

Scheme 5

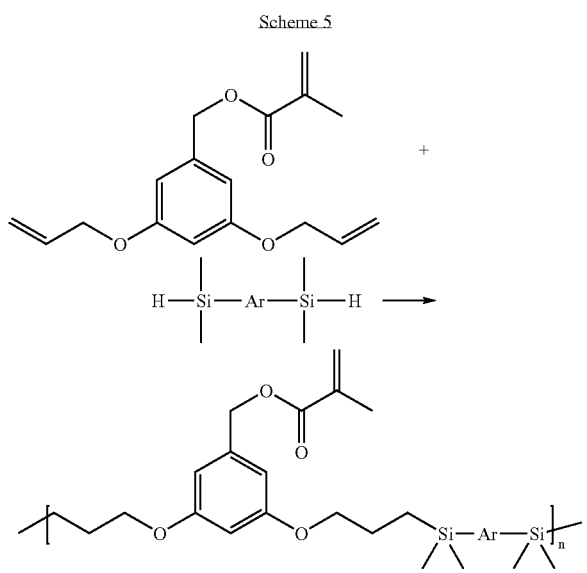

Secondary Polymerizable Materials

Additional polymerizable components other than the carbosilane polymer disclosed herein can optionally be added to the dental compositions of the present invention. These polymerizable components include one or more hardenable organic resins capable of forming a hardened material having sufficient strength and hydrolytic stability to render them suitable for use in the oral environment. Preferably, at least some of the secondary polymerizable components include ethylenic unsaturation and are capable of undergoing addition polymerization. A suitable secondary polymerizable component preferably includes at least one ethylenically unsaturated monomer (i.e., includes at least one carbon-carbon double bond).

The secondary polymerizable components of the present invention can be part of a hardenable resin. These resins are generally thermosetting materials capable of being hardened to form a polymer network including, for example, acrylate-functional materials, methacrylate-functional materials, vinyl-functional materials, and mixtures thereof. Typically, the hardenable resin is made from one or more matrix-forming oligomers, monomers, polymers, or blends thereof.

One class of hardenable resins includes materials having polymerizable components with free radically active functional groups. Examples of such materials include monomers having one or more ethylenically unsaturated groups, oligomers having one or more ethylenically unsaturated groups, polymers having one or more ethylenically unsaturated groups, and combinations thereof.

In the class of hardenable resins having free radically active functional groups, suitable polymerizable components for use in the invention contain at least one ethylenically unsaturated bond, and are capable of undergoing addition polymerization. Such free radically ethylenically unsaturated compounds include, for example, mono-, di- or poly-(meth) acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500); copolymerizable mixtures of acrylated monomers such as those in U.S. Pat. No. 4,652,274 (Boettcher et al.); acrylated oligomers such as those of U.S. Pat. No. 4,642,126 (Zador et al.); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0 373 384 (Wagenknecht et al.), EP-0 201 031 (Reiners et al.), and EP-0 201 778 (Reiners et al.). Mixtures of two or more free radically polymerizable compounds can be used if desired.

The secondary polymerizable component may also contain hydroxyl groups and free radically active functional groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis, Mo. Mixtures of ethylenically unsaturated compounds can be used if desired.

The above-listed components are typically noncrystallizable (i.e., amorphous). The secondary polymerizable component can also include a crystallizable component. This crystallizable component may or may not have a reactive group capable of polymerizing (also including crosslinking). Preferably, the crystallizable component is polymerizable. Preferably, the crystallizable component is polymeric (including oligomeric). More preferably, the crystallizable component is a polymerizable polymeric material. The secondary crystallizable polymers (including oligomers) suitable for use in the dental composition can have crystallizable main chain (i.e., linear) or pendant (i.e., side chain) segments. Preferred materials also contain reactive groups capable of polymerizing and/or crosslinking. Especially preferred are non-carbosilane crystallizable oligomers or prepolymers with a reactive functionality of at least two.

Examples of suitable secondary crystallizable materials having crystallizable main chain or backbone segments include, but are not limited to, polyesters (including polycaprolactones), polyethers, polythioethers, polyarylalkylenes, polysilanes, polyamides, polyolefins (preferably, formed from lower, e.g., C2-C3 olefins), and polyurethanes.

Preferred secondary crystallizable materials are saturated, linear, aliphatic polyester polyols (particularly diols) containing primary hydroxyl end groups. Examples of commercially available materials useful as the non-carbosilane crystallizable component in the dental compositions of the invention include some resins available under the trade designation LEXOREZ from Inolex Chemical Co., Philadelphia, Pa. Examples of other polyester polyols useful in the compositions of the invention are those available under the trade designation RUCOFLEX from Ruco Polymer Corp., Hicksville, N.Y. Examples of polycaprolactones that are useful in the invention include those available under the trade designations TONE 0230, TONE 0240, and TONE 0260 from Dow Chemical Co., Midland, Mich. Especially preferred materials are saturated, linear, aliphatic polyester polyols that are modified (e.g., through primary hydroxyl end groups) to introduce polymerizable, unsaturated functional groups, e.g., polycaprolactone diol reacted with 2-isocyanatoethyl methacrylate, methacryloyl chloride, or methacrylic anhydride.

Preferably, the total amount of the secondary polymerizable component is no greater than 60 wt-%, more preferably, no greater than 50 wt-%, and most preferably, no greater than 40 wt-%, based on the total weight of the composition.

Initiator System

Compositions of the present invention can optionally include an initiator system, i.e., one initiator or a mixture of two or more initiators, which are suitable for hardening (e.g., polymerizing and/or crosslinking) the resin system (e.g., the carbosilane-containing component and optional (meth)acrylate component). The initiator system preferably includes free radical initiators, which may be activated in a variety of ways, e.g., heat and/or radiation. Thus, for example, the initiator system can include a thermal initiator (e.g., azo compounds and peroxides), or a photoinitiator.

Preferably, the initiator system includes one or more photoinitiators. More preferably, the initiator system includes at least one photoinitiator active in the spectral region of 300 nanometers (nm) to 1200 nm and capable of promoting free radical polymerization and/or crosslinking of ethylenically unsaturated moieties upon exposure to light of suitable wavelength and intensity. A wide variety of such photoinitiators can be used. The photoinitiator preferably is soluble in the resin system. Preferably, the photoinitiator is sufficiently shelf stable and free of undesirable coloration to permit storage and use under typical dental operatory and laboratory conditions. Visible light photoinitiators are preferred.

One type of suitable initiator (i.e., initiator system) is described in U.S. Pat. No. 5,545,676 (Palazzotto et al.), which includes a three-component or ternary photoinitiator system. This system includes an iodonium salt, e.g., a diaryliodonium salt, which can be a simple salt (e.g., containing an anion such as Cl—, Br—, I—, or $C_2H_5SO_3$—) or a metal complex salt (e.g., containing $SbF_5OH$ or $AsF_6$—). Mixtures of iodonium salts can be used if desired. The second component in this ternary photoinitiator system is a sensitizer, which is capable of light absorption within the range of wavelengths of 400 nanometer (nm) to 1200 nm. The third component in this ternary photoinitiator system is an electron donor and includes amines (including aminoaldehydes and aminosilanes or other amines as described for the first initiator system), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid.

Examples of sensitizers suitable for use in a ternary photoinitiator system include ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes, and pyridinium dyes. Ketones (e.g., monoketones or alpha diketones), ketocoumarins, aminoarylketones, and p-substituted aminostyryl ketone compounds are preferred sensitizers. Examples of particularly preferred visible light sensitizers include camphorquinone, glyoxal, biacetyl, 3,3,6,6 tetramethylcyclohexanedione, 3,3,7,7-tetramethyl-1,2-cycloheptanedione, 3,3,8,8-tetramethyl-1,2-cyclooctanedione, 3,3,18,18-tetramethyl-1,2 cyclooctadecanedione, dipivaloyl, benzil, furil, hydroxybenzil, 2,3-butanedione, 2,3-pentanedione, 2,3-hexanedione, 3,4-hexanedione, 2,3-heptanedione, 3,4 heptanedione, 2,3-octanedione, 4,5-octanedione, and 1,2-cyclohexanedione. Of these, camphorquinone is the most preferred sensitizer.

Yet another type of photoinitiator includes acylphosphine oxides, such as those described in European Pat. Application No. 173567 (Ying). Suitable acylphosphine oxides are preferably of the general formula $(R^4)_2$—P(=O)—C(=O)—$R^5$, wherein each $R^4$ is individually a hydrocarbon group, preferably an alkyl group, alicyclic group, aryl group, and aralkyl group, any of which can be substituted with a halo-, alkyl- or alkoxy-group, or the two $R^4$ groups can be joined to form a ring along with the phosphorous atom, and wherein $R^5$ is a hydrocarbon group, preferably, a S-, O-, or N-containing five- or six-membered heterocyclic group, or a —Z—C(=O)—P(=O)—$(R^4)_2$ group, wherein Z represents a divalent hydrocarbon group such as alkylene or phenylene having from 2 to 6 carbon atoms. Examples of suitable acylphosphine oxides include bis(2,4,6 trimethylbenzoyl)phenyl phosphine oxide, for example. Optionally, tertiary amine reducing agents may be used in combination with an acylphosphine oxide. Illustrative tertiary amines useful in the invention include those described above as well as ethyl 4-(N,N-dimethylamino)benzoate and N,N-dimethylaminoethyl methacrylate.

Mono- and all-ketones can also be used as photoinitiators. Examples of such systems are described in U.S. Pat. No. 4,071,424 (Dart et al.).

Still another class of photoinitiators includes ionic dye-counterion complex initiators that include a borate anion and a complementary cationic dye. Borate anions useful in these photoinitiators generally can be of the formula $B(R^6)_4$— wherein each $R^6$ is independently an alkyl, aryl, alkaryl, allyl, aralkyl, alkenyl, alkynyl, alicyclic, and saturated or unsaturated heterocyclic groups. Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. Quaternary ammonium groups useful as counterions can be trimethylcetylammonium, cetylpyridinium, and tetraamethylammonium. Other organophilic cations can include pyridinium, phosphonium, and sulfonium. Cationic transition metal coordination complexes that may be useful as counterions can be complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri(2-pyridyl-s-triazine) and related ligands.

Borate salt photoinitiators are described, for example, in U.S. Pat. Nos. 4,772,530 (Gottschalkea et al.), 4,954,414 (Adair et al.), 4,874,450 (Gottschalkea), 5,055,372 (Shanklin et al.), and 5,057,393 (Shanklin et al.).

Preferred visible light-induced initiators include camphorquinone combined with a suitable hydrogen donor (e.g., an amine such as those described above for the first initiator system), and optionally a diaryliodonium simple or metal complex salt, chromophore-substituted halomethyl-s-triazine, or halomethyl oxadiazole. Particularly preferred visible light-induced photoinitiators include combinations of an alpha-diketone, e.g., camphorquinone with additional hydrogen donors, and optionally a diaryliodonium salt, e.g., diphenyliodonium chloride, bromide, iodide or hexafluorophosphate. Preferred ultraviolet light-induced polymerization initiators include ketones, such as benzyl and benzoin, acyloins, and acyloin ethers. Preferred ultraviolet light-induced polymerization initiators include 2,2-dimethoxy-2-phenylacetophenone available under the trade designation IRGACURE 651 and benzoin methyl ether (2-methoxy-2-phenylacetophenone), both from Ciba Speciality Chemicals Corp., Tarrytown, N.Y.

The initiator system is present in an amount sufficient to provide the desired rate of hardening (e.g., polymerizing and/or crosslinking). For a photoinitiator, this amount will be dependent in part on the light source, the thickness of the layer to be exposed to radiant energy, and the extinction coefficient of the photoinitiator. Preferably, the initiator system is present in a total amount of at least 0.01 wt-%, more preferably, at least 0.03 wt-%, and most preferably, at least 0.05 wt-%, based on the weight of the composition. Preferably, the initiator system is present in a total amount of no more than 10 wt-%, more preferably, no more than 5 wt-%, and most preferably, no more than 2.5 wt-%, based on the weight of the composition.

Filler System

Compositions of the present invention can optionally include a filler system (i.e., one or more fillers). Fillers for use in the filler system may be selected from a wide variety of conventional fillers for incorporation into resin systems. Preferably, the filler system includes one or more conventional materials suitable for incorporation in compositions used for medical applications, for example, fillers currently used in dental restorative compositions. Thus, the filler systems used in the compositions of the present invention are incorporated into the resin systems.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Preferred particulate filler is finely divided and has an average particle size (preferably, diameter) of less than 10 micrometers (i.e., microns).

Preferred micron-size particulate filler has an average particle size of at least 0.2 micron up to 1 micrometer. Nanoscopic particles have an average primary particle size of less than 200 nm (0.2 micron). The filler can have a unimodal or polymodal (e.g., bimodal) particle size distribution.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks. Materials of this type ("nanoscopic" materials) have average primary particle sizes (i.e., the largest dimension, e.g., diameter, of unaggregated material) of no greater than 1000 nanometers (nm). Preferably, the nanoscopic particulate material has an average primary particle size of at least 2 nanometers (nm), and preferably at least 7 nm. Preferably, the nanoscopic particulate material has an average primary particle size of no greater than 50 nm, and more preferably no greater than 20 nm in size. The average surface area of such a filler is preferably at least 20 square meters per gram ($m^2/g$), more preferably, at least 50 $m^2/g$, and most preferably, at least 100 $m^2/g$.

The filler system can include an inorganic material. It can also include a crosslinked organic material that is insoluble in the polymerizable resin, and is optionally filled with inorganic filler. The filler system is preferably generally non-toxic and suitable for use in the mouth.

Suitable fillers can be radiopaque, radiolucent, or nonradiopaque. Fillers as used in dental applications are typically ceramic in nature. Examples of suitable inorganic fillers are naturally occurring or synthetic materials such as quartz, nitrides (e.g., silicon nitride), glasses derived from, for example Ce, Sb, Sn, Zr, Sr, Ba, or Al, colloidal silica, feldspar, borosilicate glass, kaolin, talc, titania, and zinc glass, zirconia-silica fillers; and low Mohs hardness fillers such as those described in U.S. Pat. No. 4,695,251 (Randklev). Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169 (Randklev). Mixtures of these fillers can also be used, as well as combination fillers made from organic and inorganic materials.

Optionally, the surface of the filler particles may be treated with a surface treatment, such as a silane-coupling agent, in order to enhance the bond between the filler system and the resin system. The coupling agent may be functionalized with reactive curing groups, such as acrylates, methacrylates, and the like.

The filler particles used to impart a noncovalent structure can be composed of silica, alumina, zirconia, titania, or mixtures of these materials with each other or with carbon. In their synthesized state, these materials are commonly hydrophilic, due to the presence of surface hydroxyl groups. However, the materials may also be modified by treatment with appropriate agents, such as alkyl silanes, in order to modify this character. For example, the surface of a filler particle may be rendered neutral, hydrophobic, or reactive, depending on the desired properties. Fumed silica is a preferred compound for imparting self-supporting character, due to its low cost, commercial availability, and wide range of available surface character.

Other suitable fillers are disclosed in U.S. Pat. Nos. 6,387,981 (Zhang et al.) and 6,572,693 (Wu et al.) as well as International Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. patent applications entitled, "Dental Compositions Containing Nanozirconia Fillers," U.S. Ser. No. 10/847,782; "Dental Compositions Containing Nanofillers and Related Methods," U.S. Ser. No. 10/847,781; and "Use of Nanoparticles to Adjust Refractive Index of Dental Compositions," U.S. Ser. No. 10/847,803 all three of which were filed on May 17, 2004.

Preferably, the total amount of filler system is greater than 50 wt-%, more preferably, greater than 60 wt-%, and most preferably, greater than 70 wt-%, based on the total weight of the composition. If the filler system includes fibers, the fibers are present in an amount of less than 20 wt-%, based on the total weight of the composition. Preferably, the total amount of filler system is no more than 95 wt-%, and more preferably, no more than 80 wt-%, based on the total weight of the composition.

Optional Additives

The compositions of the invention may contain a surfactant system, i.e., one surfactant or a mixture of two or more surfactants. Such surfactants can be nonionic, anionic, or cationic. The surfactant(s) can be copolymerizable or non-copolymerizable.

The composition may additionally include optional agents such as colorants (e.g., pigments or dyes conventionally used for shade adjustment), flavoring agents, medicaments, stabilizers (such as butylated hydroxy toluene (BHT)), viscosity modifiers, diluting agents, flow control additives, thixotropic agents, antimicrobials, polymeric thickeners, and the like. Various combinations of these optional additives can be used if desired. Such agents may optionally include reactive functionality so that they will be copolymerized with the resin.

Preferably, the total amount of optional component is no more than 5.0 wt-%, more preferably, no more than about 2.5 wt-%, and most preferably, no more than 1.5 wt-%, based on the total weight of the composition.

Method of Use

The above described carbosilane-containing polymer can be used as a component in dental compositions that are hardenable, preferably via radical polymerization of unsaturated groups, especially (meth)acrylate groups. Dental compositions of the present invention can be used, for example, as dental restoratives or prefabricated prosthetic devices. Examples of restoratives include dental composites and amalgams. Examples of prefabricated prosthetic devices include crowns, bridges, veneers, inlays, onlays, posts, pins, and the like.

The compositions of the present invention can also be shaped (e.g., molded) into a variety of forms like three-dimensional shapes, preformed sheets, arch shaped trays, ropes, buttons, woven, or non-woven webs, and the like. The composition can be shaped (to form a first shape) in a variety of ways including, for example, extruding, injection molding, compression molding, thermoforming, vacuum forming, pressing, calendering, and web processing using rollers. Typically, a semi-finished shape is formed using a mold with a positive and negative impression. The shaped forms can be used, for example, as dental crowns, dental impression trays, and orthodontic appliances. Examples of orthodontic appliances include lingual retainers, space retainers, hooks, buttons, splints, and bases for orthodontic brackets.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

Compressive Strength (CS) Test Method

Compressive strength of a test sample was measured according to American National Standard Institute/American Standards Association (ANSI/ASA) specification No. 27 (1993). A sample was packed into a 4-millimeter (mm) (inside diameter) glass tube (and if necessary the sample was heated to accomplish the packing), and the tube was capped with silicone rubber plugs and compressed axially at approximately 0.28 megapascal (Mpa) for 5 minutes. The sample was then light cured for 90 seconds by exposure to two oppositely disposed VISILUX Model 2500 blue light guns (3M Co., St. Paul, Minn.) followed by irradiation for 180 seconds in a Dentacolor XS unit (Kulzer, Inc., Germany). Cured samples were cut with a diamond saw to form 8-mm long cylindrical plugs for measurement of compressive strength. The plugs were stored in distilled water at 37° C. for 24 hours prior to testing. Measurements were carried out on an Instron tester (Instron 4505, Instron Corp., Canton, Mass.) with a 10 kilonewton (kN) load cell at a crosshead speed of 1 mm/minute. Five cylinders of cured samples were prepared and measured with the results reported in MPa as the average of the five measurements.

Diametral Tensile Strength (DTS) Test Method

Diametral tensile strength of a test sample was measured according to ANSI/ASA specification No. 27 (1993). A sample was compressed into a glass tube and cured as described for the CS Test Method. The cured sample was then cut into 2.2-mm thick disks for measurement of DTS. The disks were stored in water as described above and measured with an Instron tester (Instron 4505, Instron Corp.) with a 10 (kN) load cell at a crosshead speed of 1 mm/minute. Five disks of cured samples were prepared and measured with results reported in MPa as the average of the five measurements.

Polymerization Shrinkage Test Method

The polymerization shrinkage of a test sample was measured using the Watts shrinkage test procedure (D. C. Watts and A. J. Cash, *Meas. Sci. Technol.*, 2, 788-794 (1991)). The test was performed using a 3-mm glass slide.

Viscosity Test Method

The viscosity of a test sample was measured using an AR 2000 Rheometer (TA Instruments, New Castle, Del.). Approximately 1.2 grams (g) of sample was placed between the stage (at 25° C.) and a 40-mm aluminum plate. The plate was rotated according to a stepped flow procedure with a log shear stress ramp from 1 to 1000 Pascals (Pa) (total of 10 data points). The viscosity results were reported in centipoises (cP) at 25° C. as the average of the 10 data points.

Abbreviations, Descriptions, and Sources of Materials

| Abbreviation | Description and Source of Material |
| --- | --- |
| BHT | 2,6-di-tert-butyl-4-methylphenol (Sigma-Aldrich, St. Louis, MO) |
| BisGMA | 2,2-Bis[4-(2-hydroxy-3-methacryloyloxypropoxy)phenyl]propane CAS No. 1565-94-2 |
| CPQ | Camphorquinone (Sigma-Aldrich) |
| EDMAB | Ethyl 4-(N,N-dimethylamino)benzoate (Sigma-Aldrich) |
| STZ | Silane-treated zirconia-silica filler prepared as described in U.S. Pat. No. 6,624,211 (Karim) |
| UDMA | Diurethane dimethacrylate (ROHAMERE 6661-0, Monomer Polymer & Dajac Labs, Inc., Feasterville, PA) |
| BisEMA-6 | Six-mole ethoxylated bisphenol A dimethacrylate (Sartomer CD541, Sartomer Co., Exton, PA) |
| DPIHFP | Diphenyl Iodonium Hexafluorophosphate (Johnson Matthey, Alpha Aesar Division, Ward Hill, NJ) |
| Benzotriazole | 2-(2-Hydroxy-5-methacryloxyethylphenyl)-2H-benzotriazole (Ciba Specialty Chemicals, Tarrytown, NJ) |
| TEGDMA | Triethyleneglycol dimethacrylate (Sigma-Aldrich) |
| TAC | Tricyclo[5.2.1.0$^{2,6}$]decanedimethanol diacrylate (Sigma-Aldrich) |

Example 1

Synthesis of Carbosilane Oligomer

Scheme 4; Ar=1,4-Disubstituted phenyl

A mixture of glycerol diallyl ether (TCI America, Portland, Oreg.) (30.00 g, 0.17 mole (mol)), methacrylic anhydride (Sigma-Aldrich) (29.55 g, 0.19 millimole (mmol)), triethylamine (Alfa Aesar, Ward Hill, Mass.) (17.76 g, 0.17 mol), 4-dimethylaminopyridine (Sigma-Aldrich) (1.05 g, 8.6 mmol), and tetrahydrofuran (70 ml) was stirred at room temperature for 4 hours. An additional charge of 4-dimethylaminopyridine (1.05 g, 8.6 mmol) was added and the mixture was stirred at room temperature for 48 hours. The reaction mixture was concentrated under vacuum and diluted with ethyl acetate (400 ml). The mixture was extracted with saturated aqueous sodium bicarbonate (200 ml) and three times with saturated aqueous sodium chloride (100 ml). The organic phase was dried over $MgSO_4$ and concentrated under vacuum. The residue was distilled under reduced pressure and two fractions were collected (60-80° C. at 0.15 mm Hg, 20 Pascals (7.48 g)) and 80-85° C. at 0.15 mm Hg, 20 Pascals (8.57 g)). The higher boiling fraction was combined with 4.6 g of the lower boiling fraction and purified by column chromatography over silica gel (30 wt % ethyl acetate in hexane) to yield 2-methylacrylic acid 2-allyloxy-1-allyloxymethyl-ethyl ester as a colorless oil (8.90 g).

A mixture of 1,4-bis-dimethylsilylbenzene (Gelest, Inc., Tulleytown, Pa.) (1.52 g, 7.9 mmol), 2-methylacrylic acid 2-allyloxy-1-allyloxymethyl-ethyl ester (2.88 g, 12 mmol), toluene (10 ml), and two drops of a solution of platinum-divinyltetramethyldisiloxane complex in xylene (Gelest, Inc.) was mixed at room temperature for 90 minutes. The mixture was loaded onto a silica gel column and eluted with a mixture of ethyl acetate (40 vol %) in hexane (60 vol %). The solvent was evaporated to yield the product as an oil (4.20 g). The viscosity of the oil was 812 cP.

Characterization of the oil by 1H Nuclear Magnetic Resonance Spectroscopy (NMR) and Infrared Spectroscopy (IR) spectra was consistent with the structure (Ar=1,4-disubstituted phenyl) shown in Scheme 4.

Example 2

Synthesis of Carbosilane Oligomer (Scheme 4; Ar=1,3-Disubstituted phenyl)

A solution of 1,3-dibromobenzene (Sigma-Aldrich) (30.00 g, 0.13 mol) in dry tetrahydrofuran (65 ml) was added dropwise over one hour to a mixture of chlorodimethylsilane (Sigma-Aldrich) (40.10 g, 0.42 mol), dry tetrahydrofuran (100 ml), and magnesium turnings (24.31 g, 0.13 mol). After full addition, the mixture was refluxed for 2 hours. The solvent was then removed under vacuum and the residue was diluted with hexane (200 ml). The solid was washed two times with hexane (200 ml) and filtered. The combined hexane solutions were concentrated under vacuum, and the residue was distilled under reduced pressure (47-49° C. at 2 mm Hg, 267 Pascals) to yield 1,3-bis-dimethylsilylbenzene as a colorless oil (17.41 g).

A mixture of 1,3-bis-dimethylsilylbenzene (1.63 g, 8.4 mmol), 2-methylacrylic acid 2-allyloxy-1-allyloxymethyl-ethyl ester (2.52 g, 12 mmol), toluene (10 ml), and two drops of a solution of platinum-divinyltetramethyldisiloxane complex in xylene was mixed at room temperature for 90 minutes. The mixture was loaded onto a silica gel column and eluted with a mixture of ethyl acetate (40 volume percent (vol %)) in hexane (60 vol %). The solvent was evaporated to yield the product as an oil (3.47 g). The viscosity of the oil was 2277 cP. Characterization of the oil by 1H NMR and IR spectra was consistent with the structure (Ar=1,3-disubstituted phenyl) shown in Scheme 4.

Example 3

Synthesis of Carbosilane Oligomer (Scheme 3; Molar Ratio A)

A mixture of bisphenol A (Sigma-Aldrich) (16.78 g, 74 mmol), allyl bromide (Sigma-Aldrich) (24.00 g, 200 mmol), potassium carbonate (Sigma-Aldrich) (30.00 g, 217 mmol), eighteen-crown-six (Sigma-Aldrich) (0.10 g), and acetone (250 ml) was mechanically stirred at 50° C. for 17 hours. The mixture was then filtered, and the filtrate concentrated under vacuum. The residue was purified by column chromatography over silica gel (10 wt % ethyl acetate in hexane) to yield bisphenol A diallyl ether as a colorless oil (20.00 g).

A mixture of bisphenol A diallyl ether (2.00 g, 6.5 mmol), 1,4-bis-dimethylsilylbenzene (2.52 g, 13 mmol), toluene (15 ml), and one drop of a solution of platinum-divinyltetramethyldisiloxane complex in xylene was mixed at room temperature for 90 minutes. Allyl methacrylate (Sigma-Aldrich) (1.64 g, 13 mmol) was added and the mixture was stirred for 3 hours. One drop of platinum-divinyltetramethyldisiloxane complex in xylene was then added and the mixture was stirred for an additional 17 hours. The mixture was loaded onto a silica gel column and eluted with a mixture of ethyl acetate (30 vol %) in hexane (70 vol %). The solvent was evaporated to yield the product as a waxy solid (4.47 g). Characterization of the waxy solid by 1H NMR and IR spectra was consistent with the structure shown in Scheme 3.

Example 4

Synthesis of Carbosilane Oligomer (Scheme 3; Molar Ratio B)

A mixture of bisphenol A diallyl ether (2.16 g, 7.0 mmol), 1,4-bis-dimethylsilylbenzene (2.52 g, 13 mmol), toluene (15 ml), and one drop of a solution of platinum-divinyltetramethyldisiloxane complex in xylene was mixed at room temperature for 90 minutes. Allyl methacrylate (Sigma-Aldrich) (1.50 g, 12 mmol) was added and the mixture was stirred for 3 hours. One drop of platinum-divinyltetramethyldisiloxane complex in xylene was then added and the mixture was stirred for an additional 17 hours. The mixture was loaded onto a silica gel column and eluted with a mixture of ethyl acetate (30 vol %) in hexane (70 vol %). The solvent was evaporated to give the product as a waxy solid (3.50 g). Characterization of the waxy solid by 1H NMR and IR spectra was consistent with the structure shown in Scheme 3.

Examples 5-12

Polymerizable Compositions

Polymerizable compositions (Examples 5-12) were prepared according to the following general procedure. The photoinitiator/stabilizer components were initially dissolved in BisGMA and the resulting mixture combined with the other monomer components of the composition (BisEMA-6, UDMA, TEGDMA, TAC, and Carbosilane Oligomer (selected from Examples 1-4)). The concentrations of photoinitiator/stabilizer components used (in terms of parts per hundred parts of BisGMA (i.e., resin), phr) were CPQ (0.176 phr), EDMAB (1.55 phr), DPIHFP (0.517 phr), BHT (0.155 phr), and Benzotriazole (1.552 phr). The blended monomer components plus the filler component STZ were weighed into a MAX 20 plastic mixing cup having a screw cap (Flakteck, Landrum, S.C.) and then the closed cup heated in an oven at 85° C. for 30 minutes. The cup was placed in a DAC 150 FV speed mixer (Flakteck) and spin mixing was carried out for 1 minute at 3000 rpm. The cup was then reheated for 30 minutes at 85° C. followed by another minute of mixing at 3000 rpm to yield the final blended compositions. The amounts of components for each example are provided in Table 1. The weight of BisGMA includes the weights of the photoinitiator/stabilizer components.

TABLE 1

| Ex. | Carbosilane Oligomer (Example) | Carbosilane Oligomer (g) | BisGMA (g) | BisEMA-6 (g) | UDMA (g) | TEGDMA (g) | TAC (g) | STZ (g) |
|---|---|---|---|---|---|---|---|---|
| 5 | 1 | 0.36 | 0.42 | 0.49 | 0.14 | 0 | 0 | 6.37 |
| 6 | 1 | 0.56 | 0.43 | 0.21 | 0 | 0.07 | 0 | 6.37 |
| 7 | 2 | 0.35 | 0.42 | 0.49 | 0.15 | 0 | 0 | 6.37 |
| 8 | 3 | 0.40 | 1.64 | 0 | 0 | 0 | 0 | 8.01 |
| 9 | 3 | 0.40 | 1.20 | 0 | 0 | 0 | 0.40 | 8.01 |
| 10 | 3 | 0.40 | 0.40 | 0.56 | 0.56 | 0.08 | 0 | 8.01 |
| 11 | 4 | 0.40 | 1.60 | 0 | 0 | 0 | 0 | 8.01 |
| 12 | 4 | 0.40 | 1.20 | 0 | 0 | 0 | 0.40 | 8.01 |

Evaluation of Composition Properties

Composition samples (Examples 5-12) were evaluated for polymerization shrinkage, compressive strength, and diametral tensile strength according to the Test Methods described herein. Results are provided in Table 2.

TABLE 2

| Example | Shrinkage (vol %) | Compressive Strength, MPa (Standard Deviation) | Diametral Tensile Strength, MPa (Standard Deviation) |
|---|---|---|---|
| 5 | 1.58 | NT* | NT |
| 6 | 1.48 | NT | NT |
| 7 | 1.40 | NT | NT |
| 8 | NT | 267 (14) | 47 (6) |
| 9 | NT | 272 (24) | 62 (9) |
| 10 | NT | 305 (22) | 72 (14) |
| 11 | NT | 266 (9) | 47 (7) |
| 12 | NT | 297 (7) | 61 (10) |

*NT—Not Tested

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A dental composition comprising:
   a carbosilane-containing polymer comprising:
      greater than one repeat unit,
      at least four Si-arylene bonds,
      at least one (meth)acrylate moiety, Si—H moiety, or both,
      no Si—O bonds, and
      two silicon atoms separated by one arylene group in each repeat unit;
   wherein the carbosilane-containing polymer has the following Formula (I):

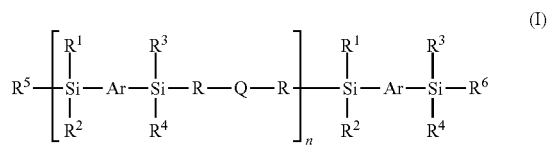

wherein:

each Ar is independently an arylene group;
each R is independently an aliphatic group, cycloaliphatic group, or combinations thereof, optionally including one or more O, Br, Cl, or Si atoms, or combinations thereof, which can include a bicyclic group;
each Q is independently a bond, or an aliphatic group, cycloaliphatic group, aromatic group, or combinations thereof, optionally including one or more O, Br, Cl, or Si atoms, or combinations thereof, which can include a bicyclic group, wherein Q optionally includes one or more (meth)acrylate groups;
each $R^1$-$R^4$ group is independently an aliphatic group, cycloaliphatic group, aromatic group, or combinations thereof, optionally substituted by one or more (meth) acrylate groups;
each $R^5$-$R^6$ group is independently hydrogen, an aliphatic group, cycloaliphatic group, aromatic group, or combinations thereof, optionally substituted by one or more (meth)acrylate groups; and
n is greater than one;
a polymerizable component different from the carbosilane-containing polymer; and
an initiator system;
wherein the carbosilane-containing polymer is polymerizable; and
wherein the dental composition is hardenable.

2. The dental composition of claim 1 wherein the carbosilane-containing polymer has at least two ethylenically unsaturated moieties.

3. The dental composition of claim 1 wherein the carbosilane-containing polymer is crystallizable.

4. The dental composition of claim 1 wherein the polymer is an oligomer having a number average molecular weight of no greater than 20,000 grams per mole.

5. The dental composition of claim 1 wherein the carbosilane-containing polymer has the following Formula (II):

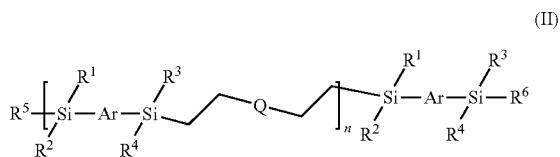

(II)

wherein:
- each Ar is independently an arylene group;
- each Q is independently a bond, or an aliphatic group, cycloaliphatic group, aromatic group, or combinations thereof, optionally including one or more O, Br, Cl, or Si atoms, or combinations thereof, which can include a bicyclic group, wherein Q is optionally substituted with one or more (meth)acrylate groups;
- each $R^1$-$R^4$ group is methyl;
- each $R^5$-$R^6$ group is independently hydrogen, an aliphatic group, cycloaliphatic group, aromatic group, or combinations thereof, optionally including one or more O, Br, Cl, or Si atoms, or combinations thereof, and optionally substituted by one or more (meth)acrylate groups; and
- n is greater than one.

6. The dental composition of claim 1 further comprising a filler system.

7. The dental composition of claim 1 further comprising an additive selected from the group consisting of a colorant, a flavoring agent, a medicament, a stabilizer, a viscosity modifier, a diluting agent, a flow control additive, a thixotropic agent, an antimicrobial, a polymeric thickener, and combinations thereof.

8. The dental composition of claim 1 wherein the polymerizable component different from the carbosilane-containing polymer is a (meth)acrylate component.

9. The dental composition of claim 1 having a polymerization shrinkage of no greater than 2.0%, based on the volume of the composition prior to hardening.

10. The dental composition of claim 1 comprising 1 wt-% to 60 wt-% of the carbosilane-containing polymer, based on the total weight of the composition.

* * * * *

UNITED STATES PATENT AND TRADEMARK OFFICE
CERTIFICATE OF CORRECTION

PATENT NO.         : 8,084,515 B2
APPLICATION NO.    : 11/571949
DATED              : December 27, 2011
INVENTOR(S)        : Lewandowski et al.

Page 1 of 1

It is certified that error appears in the above-identified patent and that said Letters Patent is hereby corrected as shown below:

Column 16
Line 8           Delete "1,2 cyclooctadecanedione," and insert
                 -- 1,2-cyclooctadecanedione, --, therefor.
Lines 49-50      Delete "tetraamethylammonium." and insert
                 -- tetramethylammonium. --, therefor.

Column 21
Line 30          Delete "Tulleytown," and insert -- Tullytown, --, therefor.

Column 23
Line 6           Delete "(Flakteck," and insert -- (Flackteck, --, therefor.
Line 9           Delete "(Flakteck," and insert -- (Flackteck, --, therefor.

Signed and Sealed this
Tenth Day of April, 2012

David J. Kappos
*Director of the United States Patent and Trademark Office*